(12) United States Patent  
Singh et al.

(10) Patent No.: US 7,579,483 B2
(45) Date of Patent: Aug. 25, 2009

(54) PROCESS FOR PREPARING 7-(ACRYLOYL)INDOLES

(75) Inventors: Jasbir Singh, Naperville, IL (US); Siead I. Zegar, Orland Park, IL (US); David E. Zembower, LaGrange, IL (US); Christopher J. Tokar, Plainfield, IL (US); Livia A. Enache, Plainfield, IL (US); Wayne E. Zeller, Viroqua, WI (US)

(73) Assignee: deCODE Genetics, ehf., Reykjavik (IS)

( * ) Notice: Subject to any disclaimer, the term of this patent is extended or adjusted under 35 U.S.C. 154(b) by 0 days.

(21) Appl. No.: 11/748,858

(22) Filed: May 15, 2007

(65) Prior Publication Data

US 2007/0270594 A1 Nov. 22, 2007

Related U.S. Application Data

(60) Provisional application No. 60/800,805, filed on May 16, 2006.

(51) Int. Cl.
 C07D 409/02 (2006.01)
 C07D 209/08 (2006.01)
(52) U.S. Cl. ..................................... 548/465
(58) Field of Classification Search ............... 548/465, 548/469
 See application file for complete search history.

(56) References Cited

U.S. PATENT DOCUMENTS

| 4,273,782 | A | 6/1981 | Cross et al. |
|---|---|---|---|
| 5,545,644 | A | 8/1996 | Macor et al. |
| 5,663,346 | A | 9/1997 | Buzzetti et al. |
| 5,994,378 | A | 11/1999 | Matsuo et al. |
| 6,166,219 | A | 12/2000 | Yamasaki et al. |
| 6,235,777 | B1 | 5/2001 | Ohuchida et al. |
| 6,242,493 | B1 | 6/2001 | Gareau et al. |
| 6,303,600 | B1 | 10/2001 | Cox et al. |
| 6,348,032 | B1 | 2/2002 | Sperl et al. |
| 6,348,474 | B1 | 2/2002 | Kayakiri et al. |
| 2006/0079520 | A1* | 4/2006 | Singh et al. ............ 514/230.5 |

FOREIGN PATENT DOCUMENTS

| EP | 0539117 A | 4/1993 |
|---|---|---|
| EP | 0620122 A | 10/1994 |
| EP | 0882718 A | 12/1998 |
| EP | 1378246 | 1/2004 |
| EP | 1431267 A | 6/2004 |

OTHER PUBLICATIONS

Hegedus et al., Palladium(0)-Catalyzed Syntheses of Indoloquinones, 1985, J. Org. Chem., 50, p. 4282.*
Heck et al., Palladium-Catalzyed Vinylic Hydrongen Substitution Reactions with Aryl, Benzyl, and Styryl Halides, 1972, J. Org. Chem., vol. 37, No. 14, p. 2321.*
Juteau et al., "Structure-Activity Relationship of Cinnamic Acylsulfonamide Analogues on the Human EP3 Prostanoid Receptor," Biorganic & Medicinal Chemistry 9, pp. 1977-1984.
Gallant et al., "Structure-Activity Relationship of Biaryl Acylsulfonamide Analogues on the Human EP3 Prostanoid Receptor," Biorganic & Medicinal Chemistry 9, pp. 2583-2586.
Dobbs, "Total Synthesis of Indoles from Tricholoma Species via Bartoli/Heteroaryl Radical Methodologies," J. Org. Chem., vol. 66, 2001, pp. 638-641.
Hegedus et al., "Palladium(0)-Catalyzed Syntheses of Indoloquinones," 1984, J. Org. Chem., 50, p. 4282.
Heck et al., "Palladium-Catalyzed Vinylic Hydrogen Substitution Reactions with Aryl, Benzyl, and Styryl Halides," 1972, J. Org. Chem., vol. 37, No. 14, p. 2321.
International Search Report and Written Opinion from International Application No. PCT/US2007/068965 completed Jul. 8, 2008 and mailed on Jul. 21, 2008.

* cited by examiner

*Primary Examiner*—Kamal A Saeed
*Assistant Examiner*—Kristin Bianchi
(74) *Attorney, Agent, or Firm*—Heslin Rothenberg Farley & Mesiti, PC

(57) ABSTRACT

The present invention involves a process for preparing substituted indoles, such as DTSI

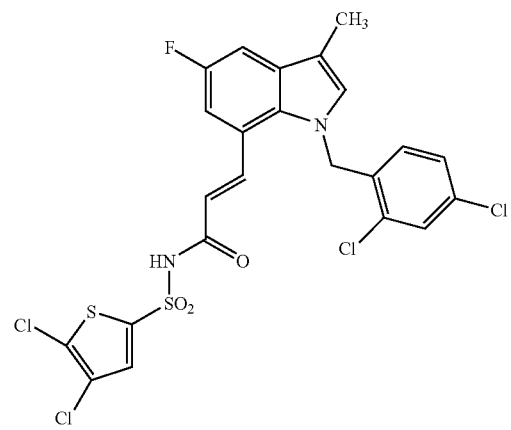

involving two sequential cross-coupling reactions.

30 Claims, No Drawings

PROCESS FOR PREPARING 7-(ACRYLOYL)INDOLES

CROSS REFERENCE TO RELATED APPLICATIONS

This application claims priority from provisional application Ser. No. 60/800,805 filed May 16, 2006, the disclosure of which is incorporated by reference herein.

FIELD OF THE INVENTION

The present invention relates to a process for preparing 7-(acryloyl)indoles.

BACKGROUND OF THE INVENTION

Atherosclerosis is the pathology underlying several of mankind's most lethal diseases, such as myocardial infarction and peripheral arterial occlusive disease (PAOD). The 7-(acryloyl)indoles prepared from this process can be used as antagonists of the $EP_3$ receptor for prostaglandin $E_2$ ($PGE_2$). Antagonists of the $EP_3$ receptor have been reported to be useful in treating (PAOD). A series of $EP_3$ antagonists has been described in U.S. application Ser. No. 11/169,161, the disclosure of which is incorporated herein by reference.

A particularly noteworthy example of an indole based therapeutic agent is 4,5-dichlorothiophene-2-sulfonic acid [(E)-3-[1-(2,4-dichlorophenylmethyl)-5-fluoro-3-methyl-1H-indol-7-yl]acryloyl]amide, or (DTSI).

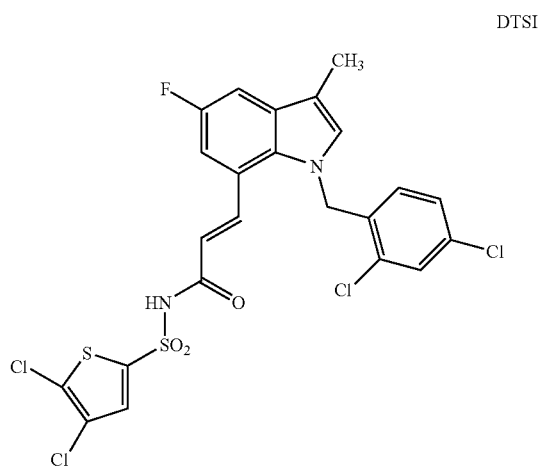

DTSI

SUMMARY OF THE INVENTION

The present invention involves a process for preparing substituted indoles involving two sequential cross-coupling reactions. Starting first with an intramolecular Heck reaction of an N-allylaniline substituted in the 2- and 6-positions with halogen or halogen equivalent [step (a)], followed by an intermolecular transition metal-catalyzed cross-coupling reaction [step (b)] between the thus-formed 7-(halo)indole with an acrylic acid, ester, or amide.

The process enables preparation of a compound of formula I

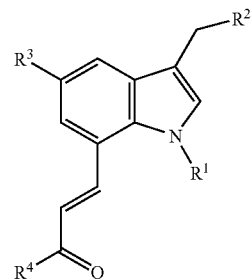

where $R^1$ is chosen from hydrogen and $C_1$-$C_{10}$ alkyl, wherein $C_1$-$C_{10}$ alkyl may be substituted with one or more substituents selected from halogen, hydroxy, alkoxy, phenoxy, nitro, cyano, carboxyl, —C(=O)O($C_1$-$C_4$)alkyl, —CONH$_2$, aryl, and heteroaryl. Said aryl or heteroaryl may be substituted with one or more of ($C_1$-$C_4$)alkyl, halogen, hydroxy, alkoxy, phenoxy, nitro, cyano, carboxyl, —C(=O)O($C_1$-$C_4$)alkyl, and —CONH$_2$. Further, $R^1$ may be chosen from aryl or heteroaryl each of which may be substituted with one or more of ($C_1$-$C_4$)alkyl, halogen, hydroxy, alkoxy, phenoxy, nitro, cyano, carboxyl, —C(=O)O($C_1$-$C_4$)alkyl, and —CONH$_2$.

$R^2$ is chosen from hydrogen, $C_1$-$C_{10}$ alkyl and $C_1$-$C_{10}$ alkyl substituted with one or more of halogen, hydroxyl, alkoxy, aryloxy, nitro, cyano, carboxyl, —C(=O)Oalkyl, —C(=O)Oaryl, —CONH$_2$, aryl, or heteroaryl. $R^2$ can also be chosen from aryl and heteroaryl, wherein each may be substituted with one or more of ($C_1$-$C_4$)alkyl, halogen, hydroxy, alkoxy, phenoxy, nitro, cyano, carboxyl, —C(=O)O($C_1$-$C_4$)alkyl, and —CONH$_2$.

$R^3$ is chosen from hydrogen, chlorine, fluorine, hydroxyl, cyano, nitro, alkoxy, aryloxy, thioalkyl, amino, aminoalkyl, aminoaryl, fluoroalkyl, $C_1$-$C_{10}$ alkyl, and $C_1$-$C_{10}$ alkyl substituted with one or more of fluorine, hydroxyl, alkoxy, aryloxy, aryl or heteroaryl.

$R^4$ is chosen from hydroxyl; $C_1$-$C_{10}$ alkoxy; $C_1$-$C_{10}$ alkoxy substituted with one or more of fluorine, alkoxy, aryloxy, aryl, or heteroaryl; and NR$^5$R$^6$. $R^5$ and $R^6$ may be different or the same and are chosen from hydrogen, or $C_1$-$C_6$ alkyl substituted with one or more of hydroxyl, alkoxy, aryloxy, nitro, cyano, carboxyl, carboxyalkyl, carboxyaryl, or carbonylamino. $R^5$ and/or $R^6$ may also be SO$_2$R$^7$ in which $R^7$ is chosen from alkyl, aryl and heteroaryl, said aryl and heteroaryl optionally substituted with one or more of halogen, hydroxy, amino, nitrile, nitro or $C_1$-$C_6$ alkyl. Alternatively, $R^5$ and $R^6$ taken together may form a monocylic 4-7 membered ring or bicyclic 8-12 membered ring.

The process comprises the steps of:
rearranging a compound of formula II

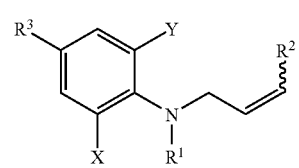

where X and Y are chosen from bromine, chlorine, iodine, and triflate, in the presence of a transition metal catalyst to form a compound of formula III

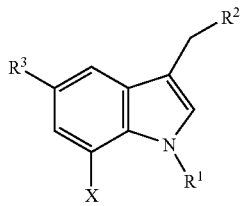

followed by reacting the compound of formula III with a compound of formula IV

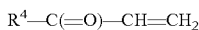

in the presence of a transition metal catalyst.

Further, the rearrangement of a compound of formula II can be carried out in the presence of a base.

The process is advantageous in that fairly complex indoles can be prepared from relatively simple components in two steps. Additionally, the two-step sequence can be combined into a one-pot operation, further increasing the utility of the process. DTSI can be prepared by such a process.

In one embodiment the invention relates to a process for preparing a compound of formula Ia:

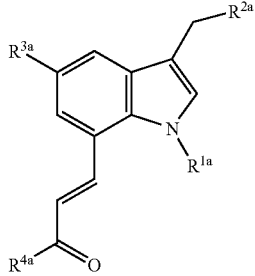

$R^{1a}$ and $R^{2a}$ are chosen from hydrogen, alkyl, benzyl and substituted benzyl. $R^{3a}$ is chosen from hydrogen, chlorine, fluorine, hydroxyl, cyano, nitro, alkoxy, aryloxy, thioalkyl, amino, aminoalkyl, aminoaryl, fluoroalkyl, and alkyl. $R^{4a}$ is chosen from hydroxyl and alkoxy, comprising the steps of rearranging a compound of formula IIa

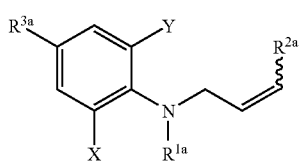

wherein X and Y are chosen from bromine, chlorine, iodine, and triflate, in the presence of a transition metal catalyst to form a compound of formula IIIa

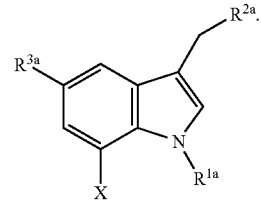

Also, the rearrangement of compound IIa can be carried out in the presence of a base.

Next, formula IIIa is reacted with a compound of formula IVa ($R^{4a}$—C(=O)—CH=CH$_2$) in the presence of a transition metal catalyst.

In a particular embodiment, the invention relates to a process for preparing DTSI

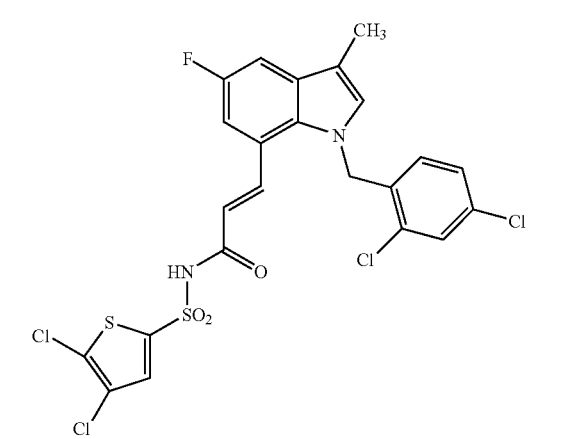

The process consists of rearranging a compound of formula IIb

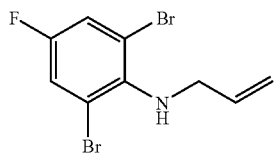

in the presence of a transition metal catalyst to form a compound of formula IIIb

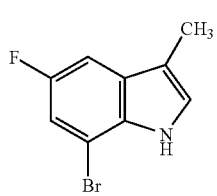

Next, a compound of formula IIIb is reacted with methyl acrylate in the presence of a transition metal catalyst to provide a compound of formula Ib

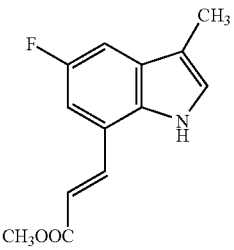

Ib

Then a compound of formula Ib is transformed to DTSI via a series of further process steps.

For example, the compound of formula Ib may be treated with a base to obtain a compound of formula Id

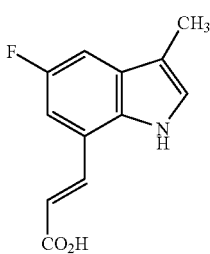

Id

Thereafter, the compound of formula Id may by reacted with 4,5-dichloro-2-thiophenesulfonamide, followed by reaction with 2,4-dichlorobenzyl chloride to obtain DTSI (see Example section). Alternatively, the compound of formula Id may by reacted with 2,4-dichlorobenzyl chloride, followed by reaction with 4,5-dichloro-2-thiophenesulfonamide to obtain DTSI (see Example section, "DTSI via an Alternative Route").

Further, DTSI can be prepared by rearranging a compound of formula IIc

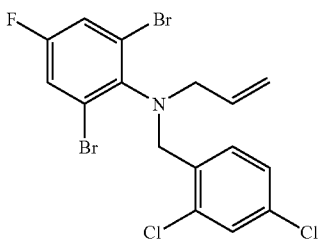

IIc in the presence of a transition metal catalyst to form a compound of formula IIIc

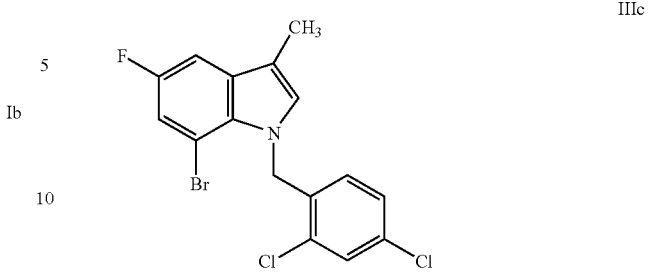

IIIc followed by reacting the compound of formula IIIc with methyl acrylate in the presence of a transition metal catalyst to provide a compound of formula Ic

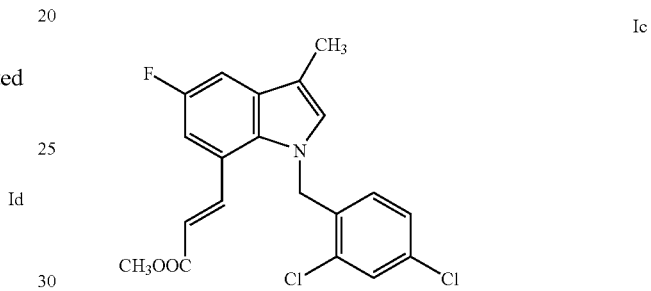

Ic

Next, a compound of formula Ic is transformed to DTSI via a series of further process steps.

For example, the compound of formula Ic may be treated with a base to convert methyl ester group into a carboxylic acid moiety. Thus obtained product may by reacted with 4,5-dichloro-2-thiophenesulfonamide to obtain DTSI (see Example section, "DTSI via an Alternative Route").

A further embodiment relates to another process for preparing DTSI. First a compound of formula IIb

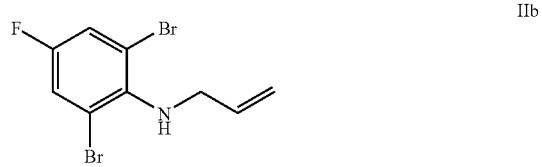

IIb is rearranged in the presence of a transition metal catalyst to form formula IIIb

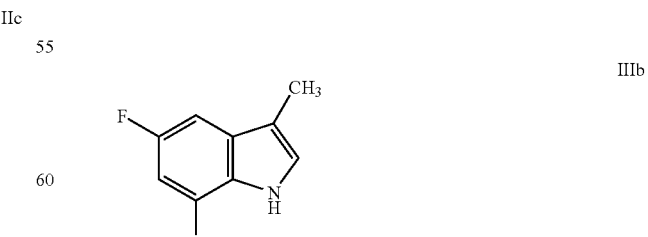

IIIb

Next, a compound of formula IIIb is reacted with acrylic acid in the presence of a transition metal catalyst to provide a compound of formula Id

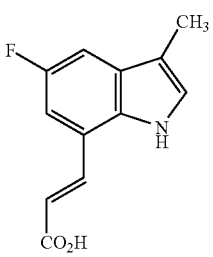

Id

Lastly, a compound of formula Id is transformed to DTSI via a series of further process steps, such as those described above.

The process of rearranging the compounds of formula IIb and formula IIc can be carried out in the presence of a base. Preferably, a base may be present when any of the compounds are being rearranged in the presence of a transition metal catalyst.

DETAILED DESCRIPTION OF THE INVENTION

Throughout this application, various references are cited. The disclosure of each of these publications in their entireties are hereby incorporated by reference as if written herein.

DEFINITIONS

The terms and substituents are defined when introduced and retain their definitions throughout.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl and alkylene groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl, adamantyl and the like. When not otherwise restricted, the term alkyl or cycloalkyl refers to alkyl of 10 or few carbons. Preferred alkyl and alkylene groups are those of $C_{10}$ or below (e.g. $C_1, C_2, C_3, C_4, C_5, C_6, C_7, C_8, C_9, C_{10}$).

$C_1$ to $C_{20}$ Hydrocarbon includes alkyl, cycloalkyl, alkenyl, alkynyl, aryl and combinations thereof. Examples include benzyl, phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons. Acylalkyl refers to a residue in which an acyl group is attached to an alkyl group which is attached to the parent. An example would be $CH_3C(\!\!=\!\!O)CH_2\!\!-\!\!$. Such residues could also be characterized as "oxoalkyl" residues.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. Aromatic 6- to 14-membered carbocyclic rings include, e.g. benzene, naphthalene, indane, tetralin, and fluorene and the 5- to 10-membered aromatic heterocyclic rings include, e.g. imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an aryl attached to the parent structure via an alkyl residue. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, loweralkyl, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr *J. Chem. Ed.* 62, 114-120 (1985), solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

The configuration of any carbon-carbon double bond appearing herein is selected for convenience only and unless explicitly stated, is not intended to designate a particular configuration. Thus the carbon-carbon double bond depicted arbitrarily above as E may be Z, E, or a mixture of the two in any proportion.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The abbreviations Me, Et, Ph, Tf, Ts and Ms represent methyl, ethyl, phenyl, trifluoromethanesulfonyl (triflate), toluenesulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The compounds of general formula IIa are readily prepared via reaction of substituted or unsubstituted anilines with allylic halides or other activated allylic radicals, including but not limited to allylic tosylates, allylic mesylates and allylic phosphates. Such allylation is preferably conducted in an organic solvent such as tetrahydrofuran, toluene, dimethylformamide, N-methylpyrrolidone or dimethylsulfoxide, using a base such as potassium t-butoxide, lithium diisopropylamide, or sodium hydride. Such allylation is conducted at temperatures ranging from about −20° C. to about the reflux temperature of the solvent. The moieties X and Y may be the same or different, but are most conveniently the same. The moieties X and Y represent halogens and other functional groups that are chemically equivalent for the purpose of cross-coupling partners for Heck reactions, typically chloride, bromide, iodide and triflate, but most commonly bromide or iodide.

The conversion of compounds of formula IIa to indoles of formula IIIa may be conducted in an organic solvent such as tetrahydrofuran, acetonitrile, toluene, dimethylformamide, N-methylpyrrolidone and dimethylsulfoxide, and commonly in acetonitrile or toluene, at a temperature ranging from about −20° C. to about the reflux temperature of the solvent. The reaction solvent may or may not contain water as a co-solvent. The transition metal catalyst is preferably present in a molar ratio ranging from about 0.1% to about 50%, and most preferably in a molar ratio of about 0.01% to about 5%. Appropriate transition metal catalysts include but are not limited to palladium, nickel, platinum, iron, cobalt, chromium, copper, and zirconium. The transition metal catalyst is preferably a palladium(II) species, including, but not limited to, $PdCl_2$, $PdBr_2$, $Pd(Acac)_2$, $PdCl_2(dppf)$, and $Pd(OAc)_2$, all of which can be reduced to Pd(0) under the conditions of the reaction, or a palladium(0) species such as $Pd(PPh_3)_4$. Coordinating ligands, if present, may include but are not limited to dppf, $PPh_3$, and $P(o\text{-tolyl})_3$. The reaction preferably contains a base including but not limited to triethylamine, potassium carbonate, cesium carbonate, diisopropylethylamine, potassium hydroxide, and sodium hydroxide. Quaternary ammonium salts such as tetrabutylammonium chloride may be added for acceleration of reaction rates (see, for example, Tuyet, J. *J. Chem. Soc. Chem. Comm.* 1984, 1287).

A compound of formula II can be produced by a process of reacting a compound of formula V

V in which W is bromine, chlorine, iodine, toluensulfonate, methanesulfonate, trifluoromethanesulfonate or methylphosphate, with an aniline of formula VI

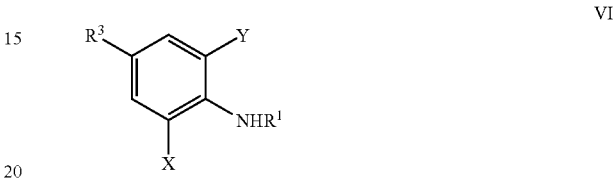

VI in the presence of a base. This base can be a trialkylamine, an alkali metal hydroxide, and an alkali metal carbonate. Examples include potassium t-butoxide, lithium dialkylamide and sodium or potassium hydride.

The indoles of formula III may be isolated and purified using chromatographic techniques such as silica gel or alumina column chromatography, high pressure liquid chromatography, or may be purified using recrystallization. Alternatively, the indoles of formula III may be converted to the 7-substituted indoles of formula I without isolation or purification. Preferably, the indoles of formula III may be prepared and subsequently converted to the 7-(acryloyl)indoles of formula I in the same reaction pot by adding reagent $R^4$—C(=O)—CH=$CH_2$, and, if necessary, additional quantities of a transition metal species, upon completion of the intramolecular Heck reaction to form formula III from formula II. It is not always necessary to add additional transition metal catalyst. Following completion of conversion of general formula II to the corresponding indole represented by formula III, addition of $R^4$—CH=$CH_2$ to the reaction mixture will often afford 7-substituted indoles of general formula I directly.

The conversion of indoles of formula III to the 7-(acryloyl) indoles of formula I may be conducted in an organic solvent such as tetrahydrofuran, acetonitrile, toluene, dimethylformamide, N-methylpyrrolidone and dimethylsulfoxide, conveniently in acetonitrile or toluene, at a temperature ranging from about −20° C. to about the reflux temperature of the solvent. The reaction solvent may or may not contain water as a co-solvent. The transition metal catalyst is preferably present in a molar ratio ranging from about 0.1% to about 50%, and most preferably in a molar ratio of about 0.01% to about 5%. The transition metal catalyst is preferably a palladium(II) species including but not limited to $PdCl_2$, $PdBr_2$, $Pd(Acac)_2$, $PdCl_2(dppf)$, and $Pd(OAc)_2$, all of which can be reduced to Pd(0) under the conditions of the reaction, or a palladium(0) species such as $Pd(PPh_3)_4$. Coordinating ligands including but not limited to dppf, $PPh_3$, or $P(o\text{-tolyl})_3$ may or may not be included in the reaction. The reaction preferably contains a base chosen from a trialkylamine, an alkali metal hydroxide, and an alkali metal carbonate.

Examples include, but are not limited to, triethylamine, potassium carbonate, cesium carbonate, diisopropylethylamine, potassium hydroxide, and sodium hydroxide. The coupling partner $R^4$—C(=O)—CH=$CH_2$ is preferably present in a molar ratio of about 0.9 to about 2.0, and most preferably in a molar ratio of about 1.0 to about 1.5, relative to the indole of formula IIIa. Quarternary ammonium salts such as tetrabutylammonium chloride may be added for acceleration of reaction rates.

The compound DTSI

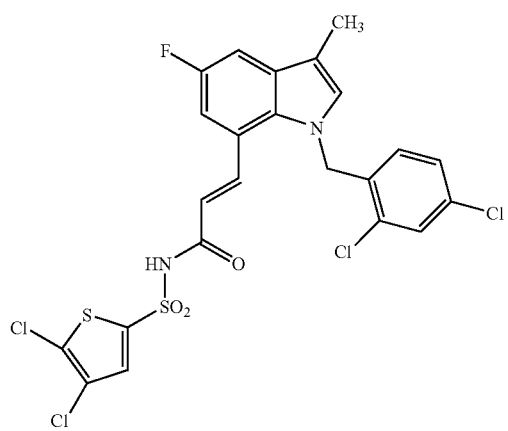

may be prepared according to an embodiment of the process of the invention by rearranging a compound of formula IIb

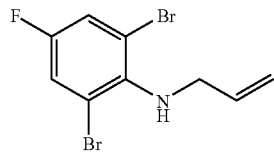

in the presence of a transition metal catalyst to form formula IIIb

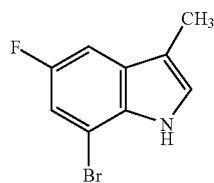

followed by reacting the compound of formula IIIb with methyl acrylate in the presence of a transition metal catalyst to provide a compound of formula Ib

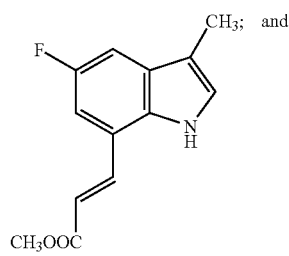

transforming the compound of formula Ib to DTSI via a series of further process steps, such as those described above.

Alternatively, DTSI may be prepared by an embodiment of the process of the invention by rearranging a compound of formula IIc

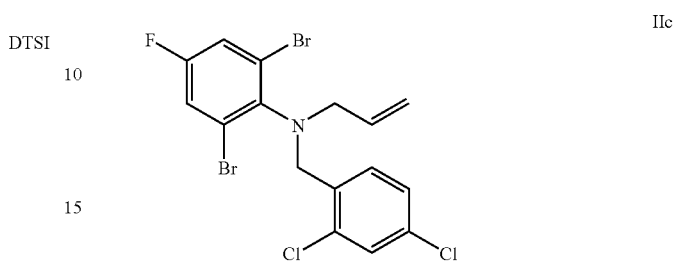

in the presence of a transition metal catalyst to form formula IIIc

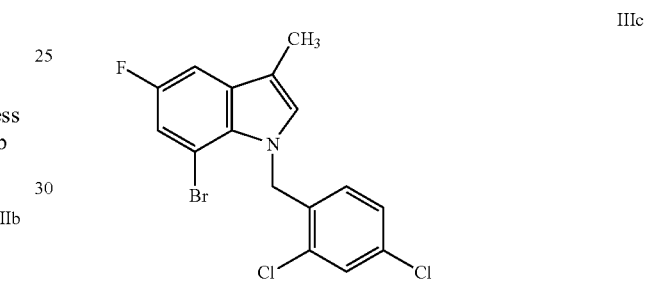

followed by reacting the compound of formula IIIc with methyl acrylate in the presence of a transition metal catalyst to provide a compound of formula Ic

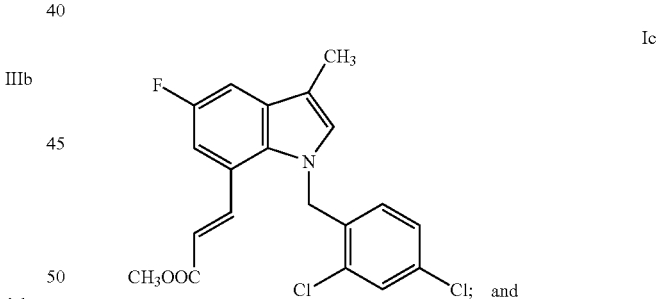

transforming the compound of formula Ic to DTSI via a series of further process steps, such as those described above.

Another embodiment relates to a further process for preparing DTSI. First, formula IIb

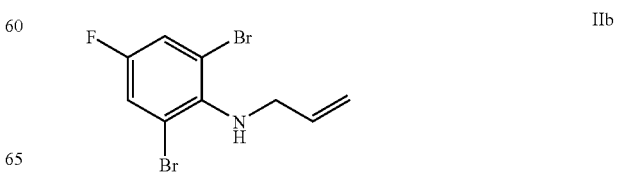

is rearranged in the presence of a transition metal catalyst to form formula IIIb

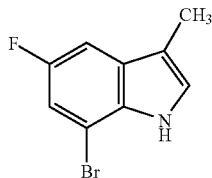

IIIb followed by reacting said compound of formula IIIb with acrylic acid in the presence of a transition metal catalyst to provide a compound of formula Id,

Id and transforming said compound of formula Id to DTSI via a series of further process steps, such as those described above.

A suitable transition metal is palladium and an exemplary transition metal catalyst is $Pd(PPh_3)_4$, $PdCl_2$, or $Pd(OAc)_2$. The rearrangement of the compound of formula IIc is carried out in the presence of a base, such as triethylamine, potassium carbonate, cesium carbonate, diisopropylethylamine, potassium hydroxide or sodium hydroxide, trialkylamine, an alkali metal hydroxide, and an alkali metal carbonate.

Compound IIc may be made by reacting the compound of formula IIb with 2,4-dichlorobenzyl halide in the presence of a base, such as KOt-Bu.

In any of the above processes the transition metals in said transition metal catalyst can be palladium, nickel, platinum, iron, cobalt, chromium, copper, or zirconium. In a preferred embodiment the transition metal is palladium. In another, the transition metal catalyst is $Pd(PPh_3)_4$, $PdCl_2$, or $Pd(OAc)_2$.

Further, formula IIb can be produced by reacting a compound of formula VIb

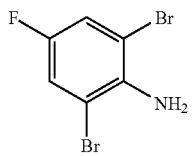

VIb with allyl halide in the presence of a base. Also, formula IIc can be produced by a process of reacting a compound of formula VIb

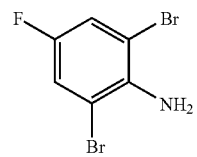

VIb with allyl halide in the presence of a base followed by alkylation with 2,4-dichlorobenzyl halide in the presence of base.

Further, a compound of formula IIc is produced by a process of reacting a compound of formula VIb

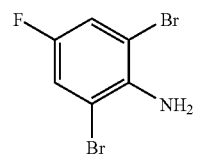

VIb with 2,4-dichlorobenzyl halide in the presence of a base followed by alkylation with allyl halide in the presence of base.

Present invention includes a process for preparing a compound of formula IIc

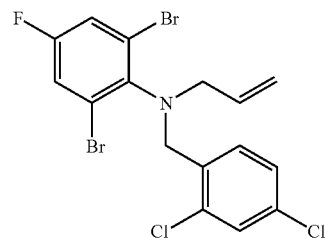

IIc comprising
(a) reacting a compound of formula VIb:

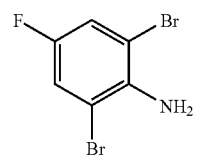

VIb with an allyl halide in the presence of base; and
(b) alkylating a product of step (a) with 2,4-dichlorobenzyl halide in the presence of a base.

In another embodiment, the invention is directed to a process for preparing a compound of formula IIc

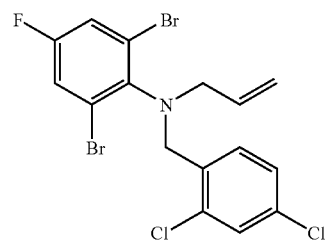

IIc comprising
(a) reacting a compound of formula VIb:

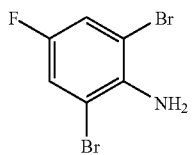

VIb with 2,4-dichlorobenzyl halide in the presence of a base; and (b) alkylating a product of step (a) with an allyl halide in the presence of base.

EXAMPLES

Example 1

Preparation of methyl 3-(5-fluoro-3-methylindol-7-yl)acrylate Via Heck Coupling with Isolation of 7-haloindole Intermediate

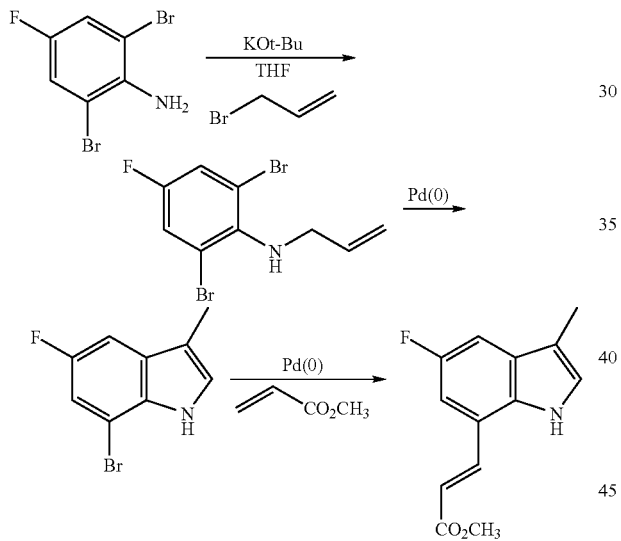

Step 1. N-Allyl-2,6-dibromo-4-fluoroaniline. 2,6-Dibromo-4-fluoroaniline (100 g, 0.372 mole) was charged into a 3-neck 3 L flask fitted with mechanical stirrer and dissolved in anhydrous tetrahydrofuran (500 mL). To this solution was charged a solution of KOtBu (1.0 M in THF, 465 mL, 0.465 mole). Allyl bromide (37 mL, 0.427 mole) was added via an addition funnel over 20 min. The mixture was stirred at ambient temperature for 14 h. The reaction mixture was diluted with MTBE (1.0 L), and water (1.0 L). The upper organic layer was separated, washed with water (2×600 mL) and brine, then dried over sodium sulfate. After filtration the solvent was removed to obtain 118 g of a brown oil. The oil was chromatographed over silica gel (500 g) and eluted with hexanes. The fractions containing the desired product were pooled and concentrated to yield 112 g (97% yield) of the desired product as a yellow oil: $^1$H NMR (CDCl3) δ 3.75 (br s, 1H), 3.79 (d, 2H, J=6.4 Hz), 5.13 (dd, 1H, J=9.6, 0.8 Hz), 5.26 (dt, 1H, J=16.8, 0.8 Hz), 5.97 (m, 1H), 7.27 (d, 2H, J=7.6 Hz).

Step 2. 7-Bromo-5-fluoro-3-methylindole. To a solution of N-Allyl-2,6-dibromo-4-fluoroaniline (20 g, 65 mmol) in 100 mL acetonitrile was added palladium(II) acetate (150 mg, 0.7 mmol), tri-O-tolylphosphine (600 mg, 2 mmol) and triethylamine (26.3 g, 260 mmol), and the resulting solution was heated at reflux for 2.5 h. The reaction was cooled to room temperature and filtered through a celite mat. The celite was rinsed with 25 mL acetonitrile, and the combined solutions were concentrated in vacuo to provide 22.5 g of crude product. The product was purified via silica gel column chromoatography to afford 11.3 g (77% yield) of the title compound: $^1$H NMR (400 MHz, CDCl$_3$) δ 2.27 (d, 3H, J=1.2 Hz), 7.06 (br s, 1H), 7.14 (dd, 1H, J=8.8, 2.4 Hz), 7.18 (dd, 1H, J=8.8, 2.4 Hz), 8.01 (br, 1H).

Step 3. Methyl 3-(5-fluoro-3-methylindol-7-yl)acrylate. To a solution of 7-bromo-5-fluoro-3-methylindole (1.145 kg, 5.02 moles) in 6.9 L acetonitrile was added methyl acrylate (904 mL, 10.04 moles), palladium(II) acetate (56.3 g, 250 mmol), tri-O-tolylphosphine (229 g, 750 mmol), and triethylamine (4.2 L, 30 moles), and the solution was heated at reflux for 16 h. After cooling to room temperature, the solution was diluted with 5.5 L water and 4.5 L MTBE. The organic phase was separated and washed with water and brine, dried over anhydrous sodium sulfate, and filtered through a celite mat. Concentration in vacuo afforded the crude product as an orange solid (1.6 kg). The solid was slurried with 3 L of hexanes for 1.5 h, then collected via filtration, rinsed with hexanes and air dried, to afford the pure title product in quantitative yield. The material could be further purified via silica gel column chromatography: $^1$H NMR (400 MHz, CDCl$_3$) δ 2.29 (d, 3H, J=1.2 Hz), 3.84 (s, 3H), 6.49 (d, 1H, J=16 Hz), 7.07 (br s, 1H), 7.15 (dd, 1H, J=10, 2.4 Hz), 7.27 (dd, 1H, J=9.2, 2.4 Hz), 7.95 (d, 1H, J=16 Hz), 8.35 (br s, 1H).

Example 2

Preparation of methyl 3-(5-fluoro-3-methylindol-7-yl)acrylate Via Heck Coupling without Isolation of 7-haloindole Intermediate

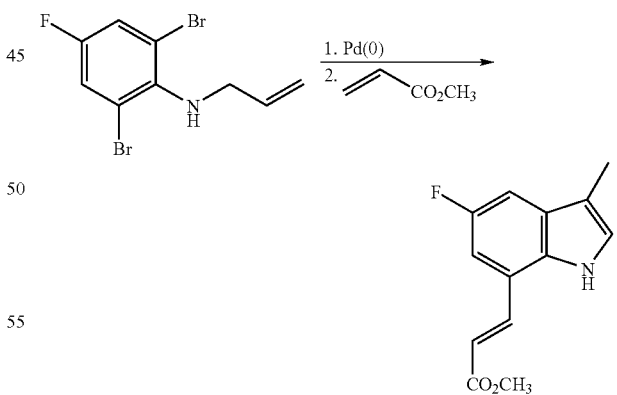

To a solution of N-allyl-2,6-dibromo-4-fluoroaniline (23.0 g, 74.4 mmol), prepared as in Step 1 of Example 1, in anhydrous acetonitrile (115 mL) in a 3-neck 250 mL flask fitted with a condenser, temperature probe, heating mantle, and nitrogen bubbler was added palladium(II) acetate (167 mg, 0.744 mmol), tri-O-tolylphosphine (906 mg, 3.0 mmol), and triethylamine (15.6 mL, 110 mmol). The dark solution was refluxed under nitrogen. After 2 h, TLC analysis indicated that the starting material was consumed. After two additional h the reaction mixture was cooled to 40° C., and the solution was charged with palladium(II) acetate (167 mg), tri-O-tolylphosphine (906 mg), triethylamine (15.6 mL), and methyl acrylate (13.4 mL, 149 mmol), and reflux was resumed. After cooling to room temperature the reaction mixture was diluted with MTBE (200 mL) and water (200 mL), and the mixture was stirred for 10 min. The dark upper organic layer was separated and washed with water (3×100 mL), brine (100 mL), and dried over sodium sulfate. After filtration the solvent was removed to obtain a tan solid. The material was dried at 50° C. for 2 h, providing 19.3 g (111%) of crude product. The crude material was suspended in a mixture of MTBE (60 mL) and hexanes (100 mL), and the mixture was refluxed for 2 h. After cooling to room temperature a gray-colored solid was collected by filtration, washed well with hexane (200 mL), and dried under vacuum at 45-50° C. for 60 hrs, providing 7.2 g of the desired product: $^1$H NMR (400 MHz, CDCl$_3$) δ 2.29 (d, 3H, J=1.2 Hz), 3.84 (s, 3H), 6.49 (d, 1H, J=16 Hz), 7.07 (br s, 1H), 7.15 (dd, 1H, J=10, 2.4 Hz), 7.27 (dd, 1H, J=9.2, 2.4 Hz), 7.95 (d, 1H, J=16 Hz), 8.35 (br s, 1H).

Example 3

Preparation of 3-(5-fluoro-3-methylindol-7-yl)acrylic Acid Via Heck Coupling without Isolation of 7-haloindole Intermediate

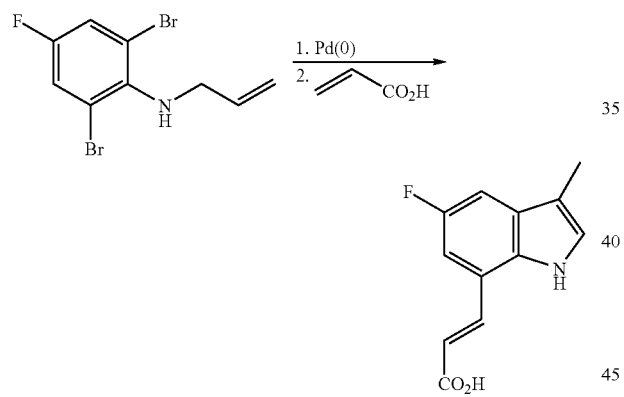

To a solution of N-allyl-2,6-dibromo-4-fluoroaniline (2.09 g, 6.76 mmol), prepared as in Step 1 of Example 1, in anhydrous acetonitrile (15 mL) was added palladium(II) acetate (31.4 mg, 0.137 mmol), tri-O-tolylphosphine (120 mg, 0.383 mmol), and triethylamine (3.8 mL, 27.3 mmol). The reaction was heated at reflux for 3 h, at which point TLC indicated consumption of starting material. The reaction was cooled to room temperature, then acrylic acid (0.56 mL, 8.08 mmol) was added via syringe and refluxing was resumed. After 3.5 h at reflux, TLC indicated reaction completion. The solution was cooled to room temperature, diluted with 21 mL water, then approximately 10 mL of the solvent was evaporated in vacuo. The solution was diluted with additional water and washed with MTBE (2×10 mL). The separated aqueous solution was acidified to pH 2-3 with 1 M HCl, which induced precipitation of the product as a yellow solid. The product was collected via suction filtration, washed with water, then vacuum dried overnight at 47° C., providing the title compound as a bright yellow solid (1.33 g, 90% yield): $^1$H NMR (400 MHz, DMSO-d$_6$) δ 2.23 (d, 3H, J=0.8 Hz), 6.67 (d, 1H, J=16 Hz), 7.24 (br s, 1H), 7.34 (dd, 1H, J=9.2, 2.4 Hz), 7.41 (dd, 1H, J=10.4, 2.4 Hz), 8.06 (dd, 1H, J=16, 1.2 Hz), 11.35 (s, 1H).

Example 4

Preparation of methyl 3-(1-(2,4-dichloro)benzyl-5-fluoro-3-methylindol-7-yl)acrylate with Isolation of 7-haloindole Intermediate

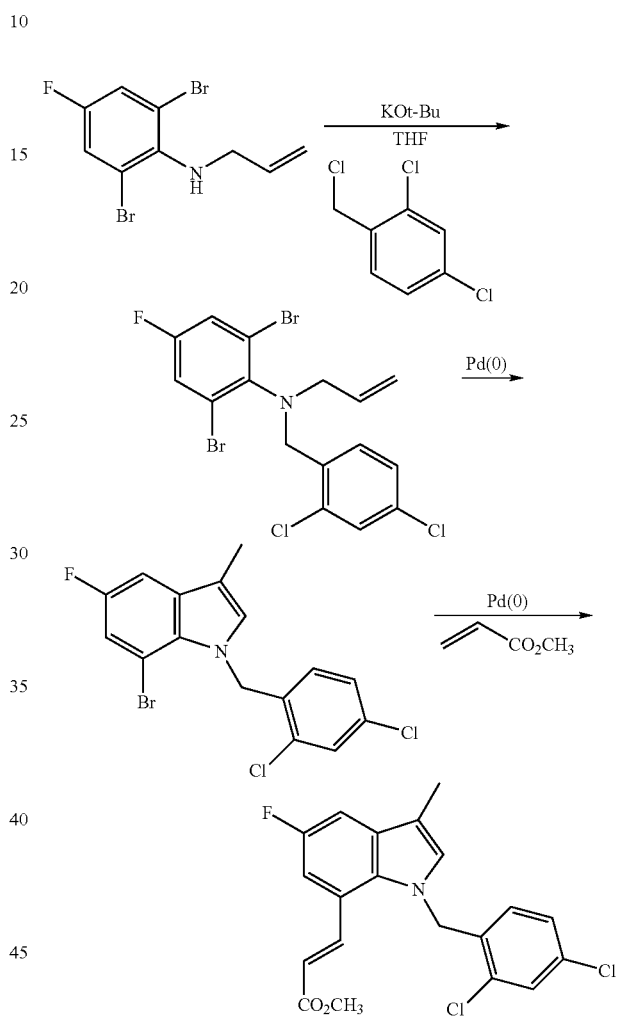

Step 1. N-Allyl-N-(2,4-dichloro)benzyl-2,6-dibromo-4-fluoroaniline. N-Allyl-2,6-dibromo-4-fluoroaniline (8.0 g, 25.9 mmol), prepared as described in Step 1 of Example 1, was dissolved in 80 mL THF. A solution of potassium t-butoxide in THF (1 M, 51.7 mmol) was added via syringe, and stirring was continued for 1 h. 2,4-Dichlorobenzyl chloride (6.1 g, 31.2 mmol) was added via syringe, and the reaction was stirred at room temperature for 24 h. The reaction mixture was diluted with ethyl acetate and washed sequentially with water and brine, dried over sodium sulfate, and concentrated to afford 10.7 g (90% yield) of the desired product as a brown semi-solid. The product could be further purified via recrystallization from methanol or acetonitrile: $^1$H NMR (400 MHz, CDCl$_3$) δ 3.77 (d, 2H, J=5.6 Hz), 4.39 (s, 2H), 5.05 (dd, 1H, J=9.6, 0.8 Hz), 5.15 (dt, 1H, J=16.8, 0.8 Hz), 5.95 (m, 1H), 7.1-7.5 (m, 5H).

Step 2. 7-Bromo-1-(2,4-dichloro)benzyl-5-fluoro-3-methylindole. To a solution of N-Allyl-N-(2,4-dichloro)benzyl-2,6-dibromo-4-fluoroaniline (10.0 g, 21 mmol) in 50 mL acetonitrile was added palladium(II) acetate (470 mg, 2 mmol), tri-O-tolylphosphine (1.92 g, 6 mmol) and triethylamine (3.19 g, 32 mmol), and the resulting solution was heated at reflux for 17 h. The reaction was cooled to room temperature and filtered through a celite mat. The solution was concentrated in vacuo and the residue was partitioned between EtOAc and water. The organic phase washed with water and brine, dried over anhydrous sodium sulfate, filtered and concentrated to provide 7.7 g of crude product. The product was purified via silica gel column chromatography with hexanes to afford 1.7 g (23% yield) of the desired product: $^1$H NMR (400 MHz, CDCl$_3$) δ 2.17 (s, 3H), 5.69 (s, 2H), 6.22 (d, 1H, J=8.4 Hz), 6.89 (s, 1H), 7.05 (dd, 1H, J=8.4, 2.0 Hz), 7.12 (dd, 1H, J=8.8, 2.4 Hz), 7.19 (dd, 1H, J=8.8, 2.4 Hz), 7.41 (d, 1H, J=2.0 Hz).

Step 3. Methyl 3-(1-(2,4-dichloro)benzyl-5-fluoro-3-methylindol-7-yl)acrylate. To a solution of 7-bromo-1-(2,4-dichloro)benzyl-5-fluoro-3-methylindole (4.1 g, 11 mmol) in 40 mL THF was added palladium(II) acetate (0.47 g, 2 mmol), tri-O-tolyl)phosphine (1.92 g, 6 mmol), and triethylamine (3.19 g, 32 mmol), and the reaction was heated at reflux for 17 h. The mixture was cooled to room temperature, filtered through a celite mat, and concentrated under reduced pressure. The residue was partitioned between EtOAc and water, and the separated organic phase washed sequentially with water and brine. The solution was dried over sodium sulfate, filtered and concentrated to afford the crude product (7.7 g). Purification via silica gel chromatography (hexanes) afforded 1.7 g (23% yield) of the desired title compound: $^1$H NMR (400 MHz, CDCl$_3$) δ 2.30 (d, 3H, J=0.8 Hz), 3.74 (s, 3H), 5.43 (s, 2H), 6.19 (d, 1H, J=15.4 Hz), 6.32 (d, 1H, J=8.8 Hz), 6.90 (br s, 1H), 7.02 (dd, 1H, J=10.0, 2.4 Hz), 7.06 (dd, 1H, J=8.6, 2.0 Hz), 7.27 (dd, 1H, J=8.6, 2.4 Hz), 7.47 (d, 1H, J=2.0 Hz), 7.75 (d, 1H, J=15.4 Hz).

Further elaboration of the products of the processes of cyclization and acrylate addition:

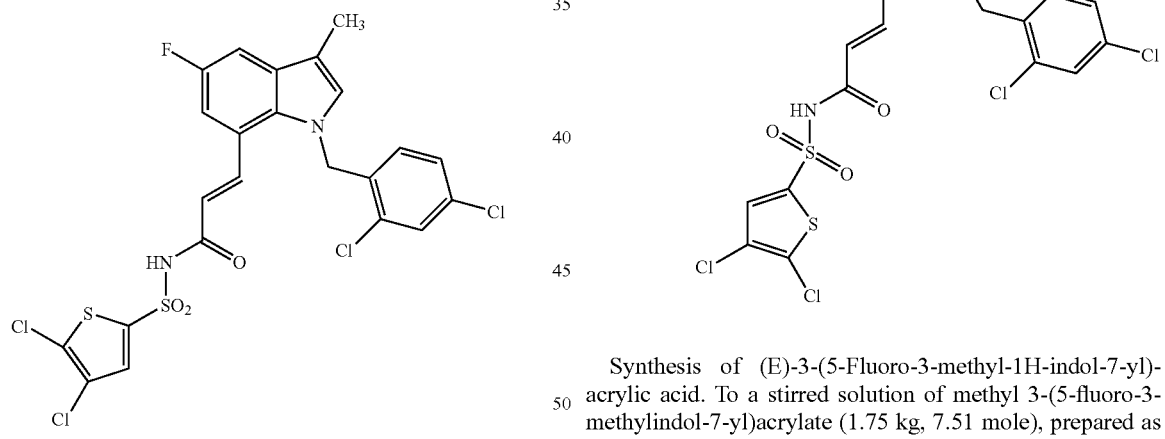

4,5-Dichloro-thiophene-2-sulfonic acid [(E)-3-[1-(2,4-dichlorophenylmethyl)-5-fluoro-3-methyl-1H-indol-7-yl]-acryloyl]amide (DTSI)

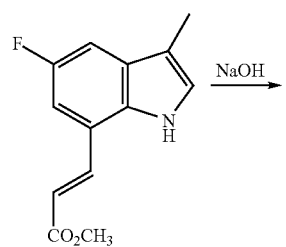

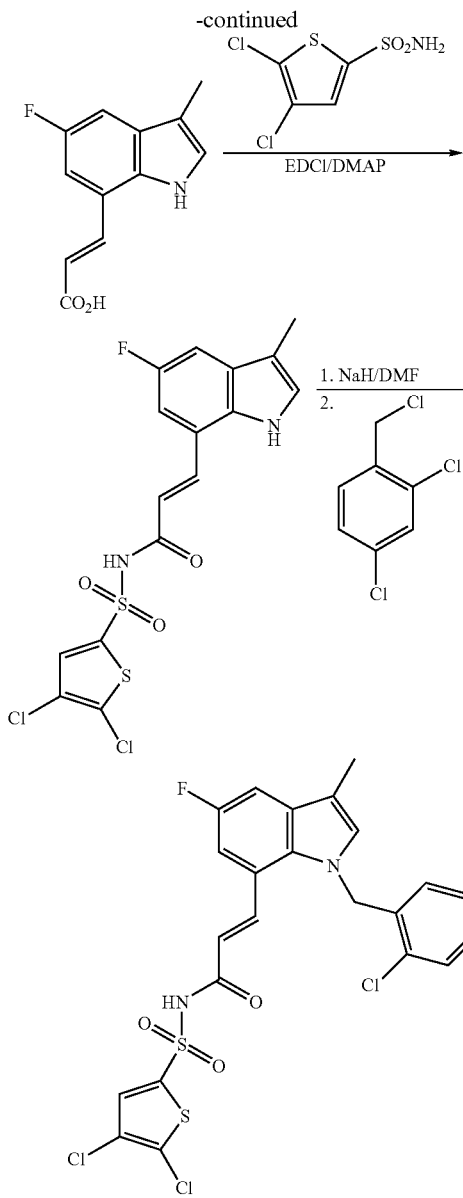

Synthesis of (E)-3-(5-Fluoro-3-methyl-1H-indol-7-yl)-acrylic acid. To a stirred solution of methyl 3-(5-fluoro-3-methylindol-7-yl)acrylate (1.75 kg, 7.51 mole), prepared as described in Example 1, in 23.4 L THF/MeOH (1:1) at room temperature was added 2 M aqueous sodium hydroxide (16.35 L, 32.7 moles). Stirring was continued for 15 h, then the reaction mixture was concentrated in vacuo to remove the volatile organic solvents. The solution was diluted with 20 L water, then extracted with dichloromethane (3×10 L). The aqueous layer was acidified to a pH of 2-3 with 2 M HCl, which induced precipitation of the product. The product was collected via vacuum filtration, washed with water (2×2 L), and vacuum dried at 60° C. to afford 1.036 kg (91% yield) of the desired title compound: $^1$H NMR (400 MHz, DMSO-d$_6$) δ 2.23 (d, 3H, J=0.8 Hz), 6.67 (d, 1H, J=16 Hz), 7.24 (br s, 1H), 7.34 (dd, 1H, J=9.2, 2.4 Hz), 7.41 (dd, 1H, J=10.4, 2.4 Hz), 8.06 (dd, 1H, J=16, 1.2 Hz), 11.35 (s, 1H).

Synthesis of 4,5-dichlorothiophene-2-sulfonic acid [(E)-3-(5-fluoro-3-methyl-1H-indol-7-yl)-acryloyl]-amide. A mixture of (E)-3-(5-fluoro-3-methyl-1H-indol-7-yl)-acrylic acid (772 g, 3.53 mole), 4,5-dichloro-2-thiophenesulfonamide (900 g, 3.88 mole), 4-(dimethylamino)pyridine (861 g, 7.06 mole) and EDCI (1.348 kg, 7.06 mole) in dichloromethane (25.5 L) was stirred at ambient temperature for 14 h. The solution was diluted with 2 M aqueous HCl (16 L), and stirred for 1.5 h, which induced precipitation of the product. The product was collected via vacuum filtration and washed sequentially with water (2×2 L), dichloromethane (2×2 L), and hexanes (2 L) to provide 1.044 kg (71% yield) of the desired title compound. $^1$H NMR (400 MHz, DMSO-$d_6$) δ 2.23 (s, 3H), 6.71 (d, 1H, J=15.6 Hz), 7.22 (dd, 1H, J=10.0, 2.6 Hz), 7.27 (br s, 1H), 7.39 (dd, 1H, J=9.6, 2.6 Hz), 7.95 (s, 1H), 8.15 (dd, 1H, J=15.6, 1.2 Hz), 11.35 (s, 1H).

Synthesis of 4,5-dichloro-thiophene-2-sulfonic acid [(E)-3-[1-(2,4-dichlorophenylmethyl)-5-fluoro-3-methyl-1H-indol-7-yl]-acryloyl]amide (DTSI). To a solution of 4,5-dichlorothiophene-2-sulfonic acid [(E)-3-(5-fluoro-3-methyl-1H-indol-7-yl)-acryloyl]-amide (1.025 kg, 2.37 mole) in DMF (5.1 L) at 0° C. was added NaH (60% in oil, 353 g, 8.8 mole) portionwise and the reaction mixture was allowed to stir for 30 min. 2,4-Dichlorobenzyl chloride (924 g, 1.41 mole) was added at such a rate to maintain the temperature near 0° C. After stirring about 45 min, the reaction mixture was carefully quenched with water (15 L), then diluted with 2 M HCl (9 L) and dichloromethane (10 L), which led to precipitation of the desired title product. The precipitated product was collected via vacuum filtration and the filter cake washed sequentially with water (2×2 L), and cold EtOH (2×1 L). The product was vacuum dried at 60° C. to afford 1.305 kg (93% yield) of desired product, as a solvate with DMF. The product was recrystallized from absolute EtOH to afford the pure product: $^1$H-NMR (400 MHz, DMSO-$d_6$) δ 2.26 (s, 3H), 5.53 (s, 2H), 6.12 (d, 1H, J=8.4 Hz), 6.21 (d, 1H, J=15.4 Hz), 7.04 (dd, 1H, J=10.0, 2.4 Hz), 7.22 (dd, 1H, J=8.4, 2.0 Hz), 7.37 (s, 1H), 7.38 (d, 1H, J=2.0 Hz), 7.46 (dd, 1H, J=9.2, 2.4 Hz), 7.74 (d, 1H, J=15.4 Hz), 7.90 (s, 1H).

DTSI Via an Alternative Route

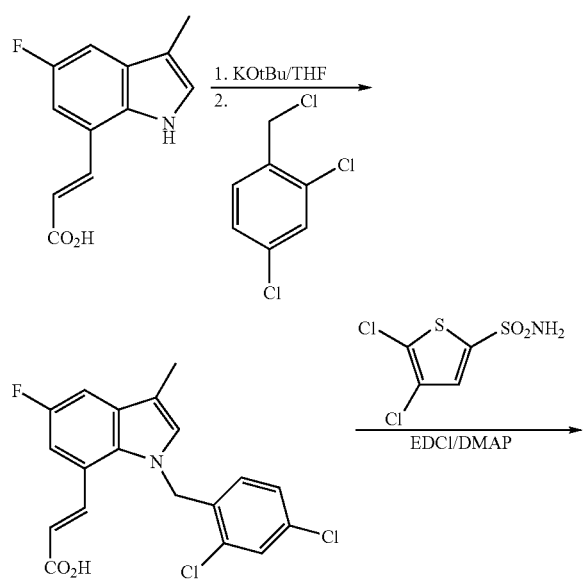

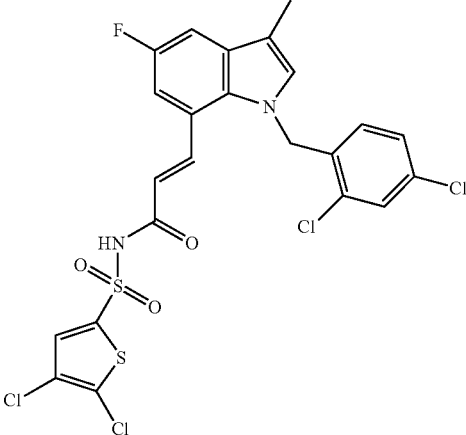

Synthesis of (E)-3-[1-(2,4-Dichlorobenzyl)-5-fluoro-3-methyl-1H-indol-7-yl]-acrylic acid. To a solution of 3-(5-fluoro-3-methylindol-7-yl)acrylic acid, prepared as in Example 3 (20 g, 92 mmol) in 200 mL THF was added potassium t-butoxide (24.4 g, 206 mmol) in portions over approximately 10 min, while keeping the internal temperature below 18° C. with an ice-water bath. 2,4-Dichlorobenzyl chloride (21.7 g, 110 mmol) was added over a period of 5 min, after which the cooling bath was removed. The reaction mixture was stirred for 24 h, then quenched with 200 mL water, followed by dilution with 200 mL MTBE and 200 mL heptanes. After stirring for 10 min, the layers were separated, and the aqueous layer was filtered through a celite pad. The pad was rinsed with 50 mL water, and the aqueous filtrate was acidified to pH of 1-2 with 2 M HCl. The suspension was diluted with 200 mL MTBE and 100 mL heptanes, stirred for 5 min, then the solids were collected on a fritted glass funnel and rinsed with heptanes. The solids were dried under reduced pressure overnight at 58° C. to afford 24.4 g (70% yield) of the title compound: $^1$H-NMR (400 MHz, DMSO-$d_6$) δ 2.26 (s, 3H), 5.55 (s, 2H), 6.21 (d, 1H, J=8.4 Hz), 6.24 (d, 1H, J=15.6 Hz), 7.22 (dd, 1H, J=10.4, 2.4 Hz), 7.28 (dd, 1H, J=8.6, 2.0 Hz), 7.34 (s, 1H), 7.43 (dd, 1H, J=8.6, 2.4 Hz), 7.66 (d, 1H, J=15.6 Hz), 7.67 (d, 1H, J=2.4 Hz), 12.29 (s, 1H).

Alternative Synthesis of (E)-3-[1-(2,4-Dichlorobenzyl)-5-fluoro-3-methyl-1H-indol-7-yl]-acrylic acid. To a solution of methyl 3-(1-(2,4-dichloro)benzyl-5-fluoro-3-methylindol-7-yl)acrylate, prepared as described in Example 4 (0.80 g, 2.4 mmol) in a 1:1 solution of MeOH/THF (20 mL) was added a solution of 2 M aqueous NaOH (10 mL, 20 mmol), and the solution was stirred at room temperature for 16 h. The solvent volume was concentrated under vacuum to remove the volatile organics, and the resulting solution was diluted with 20 mL water and 30 mL isopropyl acetate. The organic phase was separated, washed with water and brine, then dried over sodium sulfate and filtered. The pH of the organic layer was adjusted to approximately 2 with 2 M HCl in ether, then re-washed successively with water and brine. After drying over sodium sulfate, the solution was filtered and concentrated to afford the desired product as a bright yellow solid (0.67 g, 85% yield): $^1$H-NMR (400 MHz, DMSO-$d_6$) δ 2.26 (s, 3H), 5.55 (s, 2H), 6.21 (d, 1H, J=8.4 Hz), 6.24 (d, 1H, J=15.6 Hz), 7.22 (dd, 1H, J=10.4, 2.4 Hz), 7.28 (dd, 1H, J=8.6, 2.0 Hz), 7.34 (s, 1H), 7.43 (dd, 1H, J=8.6, 2.4 Hz), 7.66 (d, 1H, J=15.6 Hz), 7.67 (d, 1H, J=2.4 Hz), 12.29 (s, 1H).

Synthesis of 4,5-Dichloro-thiophene-2-sulfonic acid [(E)-3-[1-(2,4-dichlorophenylmethyl)-5-fluoro-3-methyl-1H-indol-7-yl]-acryloyl]amide (DTSI). To a solution of (E)-3-[1-(2,4-dichloro-benzyl)-5-fluoro-3-methyl-1H-indol-7-yl]-acrylic acid (10.0 g, 26.4 mmol) in dichloromethane (100 mL) was added EDCI (7.9 g, 41.2 mmol), HOBt hydrate (0.71 g, 5.3 mmol), and diisopropylethylamine (10.6 g, 81.8 mmol), and the mixture was stirred for 20 mm. To the reaction was added 4,5-dichlorothiophene-2-sulfonamide (6.43 g, 27.2 mmol), and the mixture was stirred at room temperature for 15 mm, then at reflux for 16 h. The reaction was cooled to room temperature then diluted with 25 mL water followed by 25 mL 2 M HCl. The mixture was stirred for 5 mm, then the phases were split. The organic phase was diluted with 25 mL of 2 M HCl and stirred, which induced precipitation of the product. The temperature was reduced to 0° C., and stirring was continued for 1 h. The product was collected via vacuum filtration, washed with water (3×25 mL) and heptanes (2×25 mL), then vacuum dried at 60° C. to afford 9.3 g (60% yield) of the title compound. The product could be further purified via recrystallization from ethanol: $^1$H-NMR (400 MHz, DMSO-$d_6$) δ 2.26 (s, 3H), 5.53 (s, 2H), 6.12 (d, 1H, J=8.4 Hz), 6.21 (d, 1H, J=15.4 Hz), 7.04 (dd, 1H, J=10.0, 2.4 Hz), 7.22 (dd, 1H, J=8.4, 2.0 Hz), 7.37 (s, 1H), 7.38 (d, 1H, J=2.0 Hz), 7.46 (dd, 1H, J=9.2, 2.4 Hz), 7.74 (d, 1H, J=15.4 Hz), 7.90 (s, 1H).

What is claimed is:

1. A process for preparing a compound of formula I:

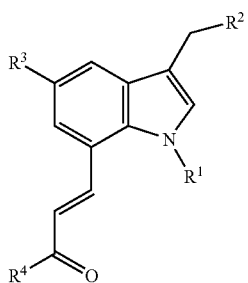

I wherein $R^1$ is chosen from:
hydrogen;
$C_1$-$C_{10}$ alkyl;
$C_1$-$C_{10}$ alkyl substituted with one or more of halogen, hydroxy, alkoxy, phenoxy, nitro, cyano, carboxyl, —C(=O)O($C_1$-$C_4$)alkyl, —CONH$_2$, aryl, or heteroaryl; said aryl or heteroaryl substituted with one or more of ($C_1$-$C_4$)alkyl, halogen, hydroxy, alkoxy, phenoxy, nitro, cyano, carboxyl, —C(=O)O($C_1$-$C_4$)alkyl, and —CONH$_2$;
aryl and aryl substituted with one or more of ($C_1$-$C_4$) alkyl, halogen, hydroxy, alkoxy, phenoxy, nitro, cyano, carboxyl, —C(=O)O($C_1$-$C_4$)alkyl, and —CONH$_2$; and
heteroaryl and heteroaryl substituted with one or more of ($C_1$-$C_4$)alkyl, halogen, hydroxy, alkoxy, phenoxy, nitro, cyano, carboxyl, —C(=O)O($C_1$-$C_4$)alkyl, and —CONH$_2$;

$R^2$ is chosen from:
hydrogen;
$C_1$-$C_{10}$ alkyl and $C_1$-$C_{10}$ alkyl substituted with one or more of halogen, hydroxyl, alkoxy, aryloxy, nitro, cyano, carboxyl, —C(=O)Oalkyl, —C(=O)Oaryl, —CONH$_2$, aryl, or heteroaryl;
aryl and aryl substituted with one or more of ($C_1$-$C_4$) alkyl, halogen, hydroxy, alkoxy, phenoxy, nitro, cyano, carboxyl, —C(=O)O($C_1$-$C_4$)alkyl, and —CONH$_2$; and
heteroaryl and heteroaryl substituted with one or more of ($C_1$-$C_4$)alkyl, halogen, hydroxy, alkoxy, phenoxy, nitro, cyano, carboxyl, —C(=O)O($C_1$-$C_4$)alkyl, and —CONH$_2$;

$R^3$ is chosen from:
hydrogen, chlorine, fluorine, hydroxy, cyano, nitro, alkoxy, aryloxy, thioalkyl, amino, aminoalkyl, aminoaryl, fluoroalkyl, $C_1$-$C_{10}$ alkyl, $C_1$-$C_{10}$ alkyl substituted with one or more of fluorine, hydroxyl, alkoxy, aryloxy, aryl or heteroaryl;

$R^4$ is chosen from:
hydroxyl;
$C_1$-$C_{10}$ alkoxy;
$C_1$-$C_{10}$ alkoxy substituted with one or more of fluorine, alkoxy, aryloxy, aryl, or heteroaryl;
$NR^5R^6$, where $R^5$ and $R^6$ are the same or different and are chosen from hydrogen;
$C_1$-$C_6$ alkyl substituted with one or more of halogen, hydroxyl, alkoxy, aryloxy, nitro, cyano, carboxyl, carboxyalkyl, carboxyaryl, or carbonylamino; and
$SO_2R^7$ in which $R^7$ is chosen from alkyl, aryl and heteroaryl, said aryl and heteroaryl substituted with one or more of halogen, hydroxy, amino, nitrile, nitro or $C_1$-$C_6$ alkyl; or
$R^5$ and $R^6$ taken together form a monocylic 4-7 membered ring or bicyclic 8-12 membered ring;

said process comprising the steps of:
a) rearranging a compound of formula II

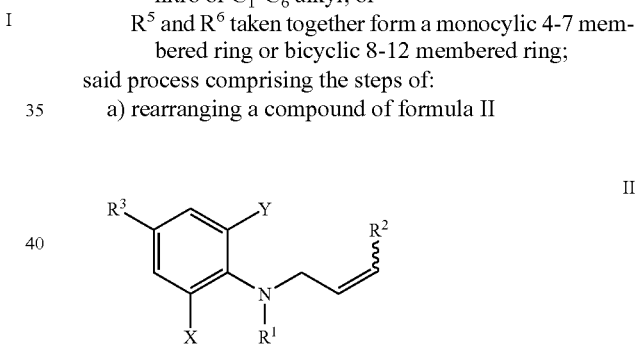

II wherein

X and Y are independently chosen from bromine, chlorine, iodine, and triflate;

in the presence of a transition metal catalyst to form a compound of formula III

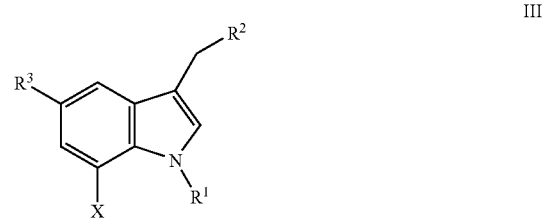

III b) followed by reacting said compound of formula III with a compound of formula IV $R^4$—C(=O)—CH=CH$_2$ (IV)

in the presence of a transition metal catalyst.

2. A process for preparing a compound of formula Ia:

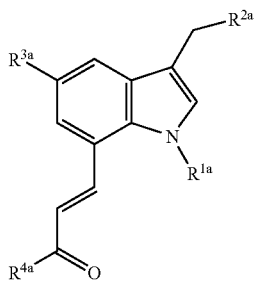

wherein
$R^{1a}$ and $R^{2a}$ are chosen from hydrogen, alkyl, benzyl and substituted benzyl;
$R^{3a}$ is chosen from hydrogen, chlorine, fluorine, hydroxyl, cyano, nitro, alkoxy, aryloxy, thioalkyl, amino, aminoalkyl, aminoaryl, fluoroalkyl, and alkyl; and
$R^{4a}$ is chosen from hydroxyl and alkoxy;
comprising the steps of:
a) rearranging a compound of formula IIa

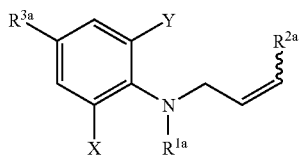

wherein
X and Y are chosen from bromine, chlorine, iodine, and triflate;
in the presence of a transition metal catalyst to form a compound of formula IIIa

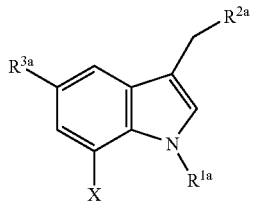

b) followed by reacting said compound of formula IIIa with a compound of formula IVa

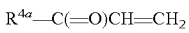    (IVa)

in the presence of a transition metal catalyst.

3. A process according to claim 1 wherein the transition metal in said transition metal catalyst is palladium, nickel, platinum, iron, cobalt, chromium, copper, or zirconium.

4. A process according to claim 3 wherein said transition metal is palladium.

5. A process according to claim 1 wherein said transition metal catalyst is $Pd(PPh_3)_4$, $PdCl_2$, or $Pd(OAc)_2$.

6. A process according to claim 1 wherein said rearrangement of said compound of formula II is carried out in the presence of a base.

7. A process according to claim 1 wherein said reaction of said compound of formula III with said compound of formula IV is carried out in the presence of a base.

8. A process according to claim 6 wherein base is chosen from a trialkylamine, an alkali metal hydroxide, and an alkali metal carbonate.

9. A process according to claim 7 wherein said base is chosen from a trialkylamine, an alkali metal hydroxide, and an alkali metal carbonate.

10. A process according to claim 6 wherein said base is chosen from triethylamine, potassium carbonate, cesium carbonate, diisopropylethylamine, potassium hydroxide, and sodium hydroxide.

11. A process according to claim 7 wherein said base is chosen from triethylamine, potassium carbonate, cesium carbonate, diisopropylethylamine, potassium hydroxide, and sodium hydroxide.

12. A process according to claim 1 wherein said compound of formula II is produced by a process of reacting a compound of formula V:

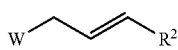

wherein W is chosen from bromine, chlorine, iodine, toluensulfonate, methanesulfonate, trifluoromethanesulfonate and methyl phosphate, with an aniline of formula VI:

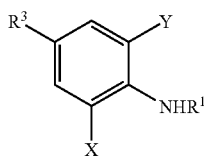

in the presence of a base.

13. A process according to claim 2 wherein said compound of formula IIa is produced by a process of reacting a compound of formula Va:

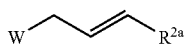

wherein W is chosen from bromine, chlorine, iodine, and triflate; with an aniline of formula VIa

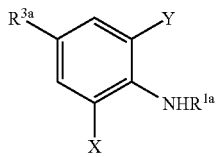

in the presence of a base.

14. A process according to claim 12 wherein said base is chosen from potassium t-butoxide, lithium dialkylamide and sodium or potassium hydride.

15. A process according to claim 12 wherein W is bromine.

16. A process for preparing DTSI:

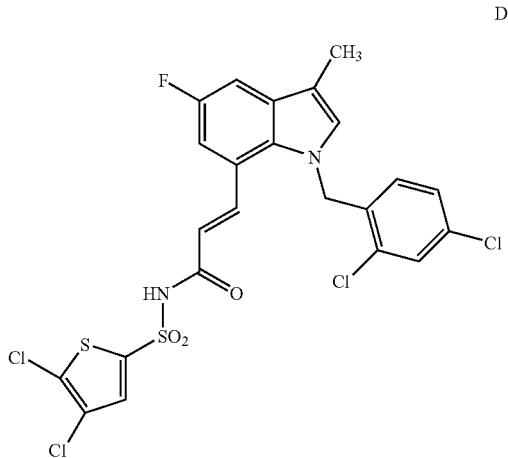

comprising the steps of:
 a) rearranging a compound of formula IIb

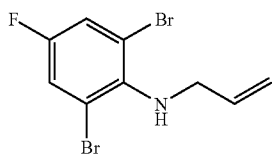

in the presence of a transition metal catalyst to form formula IIIb

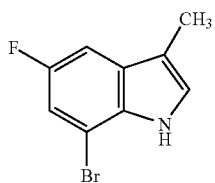

b) followed by reacting said compound of formula IIIb with methyl acrylate in the presence of a transition metal catalyst to provide a compound of formula Ib

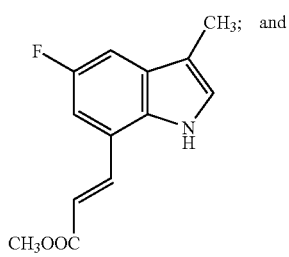

c) transforming said compound of formula Ib to DTSI via a series of further process steps.

17. A process for preparing DTSI:

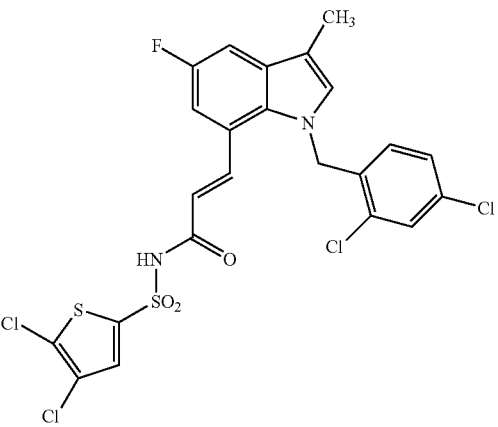

comprising the steps of:
 a) rearranging a compound of formula IIc

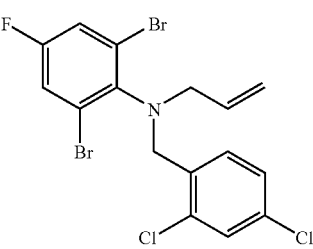

in the presence of a transition metal catalyst to form formula IIIc

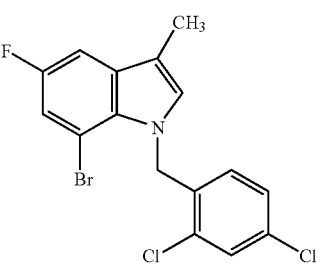

b) followed by reacting the compound of formula IIIc with methyl acrylate in the presence of a transition metal catalyst to provide a compound of formula Ic

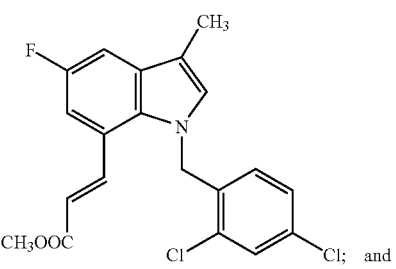

c) transforming the compound of formula Ic to DTSI via a series of further process steps.

18. A process for preparing DTSI:

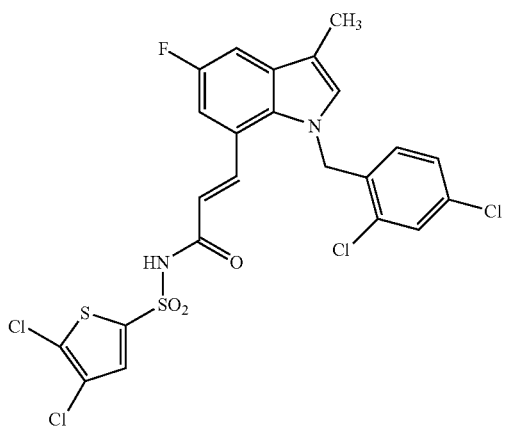

comprising the steps of:
a) rearranging a compound of formula IIb

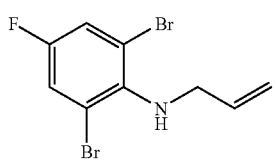

in the presence of a transition metal catalyst to form formula IIIb

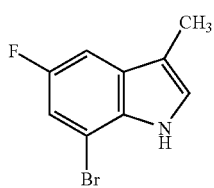

b) followed by reacting said compound of formula IIIb with acrylic acid in the presence of a transition metal catalyst to provide a compound of formula Id

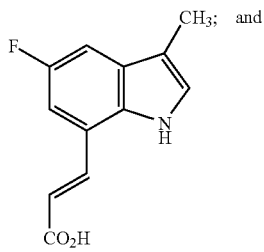

c) transforming said compound of formula Id to DTSI via a series of further process steps.

19. A process according to claim 16 wherein the transition metal in said transition metal catalyst is palladium, nickel, platinum, iron, cobalt, chromium, copper, or zirconium.

20. A process according to claim 19 wherein said transition metal is palladium.

21. A process according to claim 16 wherein said transition metal catalyst is $Pd(PPh_3)_4$, $PdCl_2$, or $Pd(OAc)_2$.

22. A process according to claim 16 wherein said rearrangement of said compound of formula IIb and formula IIc is carried out in the presence of a base.

23. A process according to claim 22 wherein said base is chosen from a trialkylamine, an alkali metal hydroxide, and an alkali metal carbonate.

24. A process according to claim 22 wherein said base is chosen from triethylamine, potassium carbonate, cesium carbonate, diisopropylethylamine, potassium hydroxide, and sodium hydroxide.

25. A process according to claim 16 wherein said compound of formula IIb is produced by a process of reacting a compound of formula VIb:

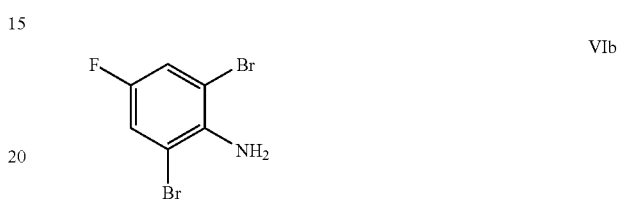

with allyl halide in the presence of a base.

26. A process according to claim 18 wherein said compound of formula IIb is produced by a process of reacting a compound of formula VIb:

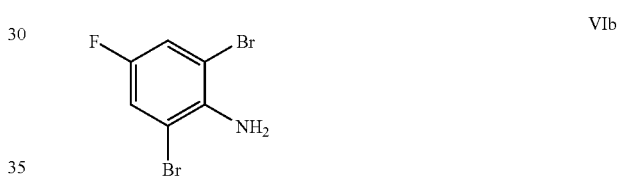

with allyl halide in the presence of a base.

27. A process according to claim 17 wherein said compound of formula IIc is produced by a process of reacting a compound of formula VIb:

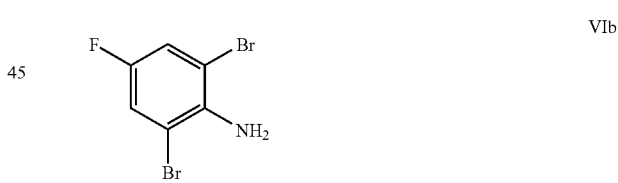

with allyl halide in the presence of a base followed by alkylation with 2,4-dichlorobenzyl halide in the presence of base.

28. A process according to claim 17 wherein said compound of formula IIc is produced by a process comprising
(a) reacting a compound of formula VIb:

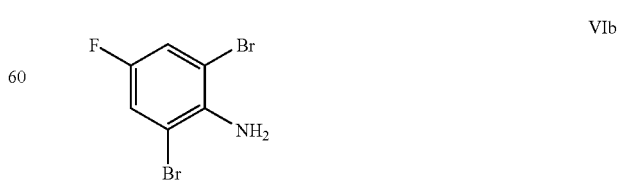

with 2,4-dichlorobenzyl halide in the presence of a base; and (b) alkylating a product of step (a) with an allyl halide in the presence of base.

29. A process for preparing DTSI:

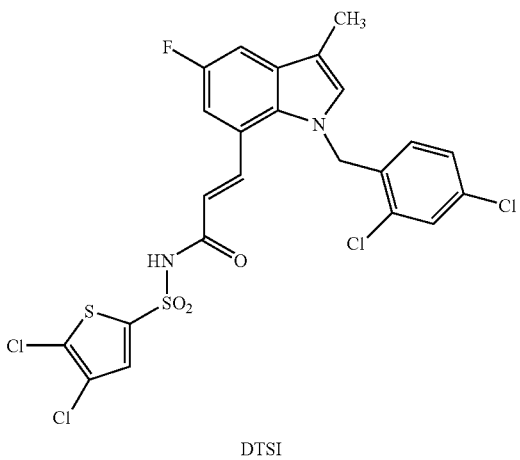

DTSI comprising the steps of:
(a) bringing together a compound of formula IIb

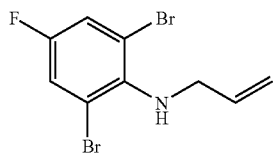

in the presence of a palladium catalyst with acrylic acid to form a compound of formula Id

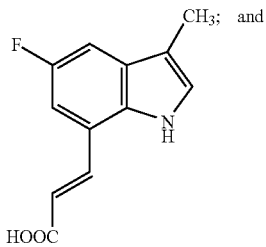

(b) transforming said compound of formula Id to DTSI via a series of further process steps.

30. A process according to claim 29 wherein said further process steps include:
(a) reacting said compound of formula Id with 2,4-dichlorobenzyl chloride to provide an N-benzyl indole of formula:

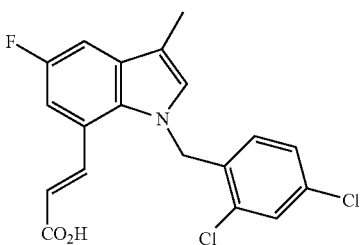

(b) reacting said N-benzyl indole with 4,5-dichlorothiophene-2-sulfonamide to provide DTSI.

* * * * *

UNITED STATES PATENT AND TRADEMARK OFFICE
CERTIFICATE OF CORRECTION

PATENT NO. : 7,579,483 B2 Page 1 of 1
APPLICATION NO. : 11/748858
DATED : August 25, 2009
INVENTOR(S) : Singh et al.

It is certified that error appears in the above-identified patent and that said Letters Patent is hereby corrected as shown below:

Col. 26 Line 42-52 Claim 13 should read: A process according to claim 2 wherein said compound of formula IIa is produced by a process of reacting a compound of formula Va:

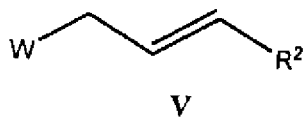

V wherein W is chosen from bromine, chlorine, iodine, and triflate; with an aniline of formula VIa

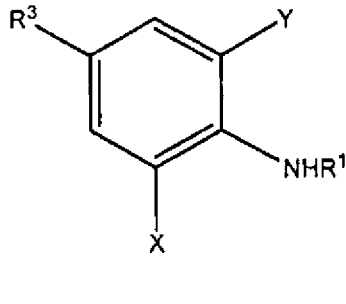

VI in the presence of a base.

Signed and Sealed this

Eighth Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,579,483 B2
APPLICATION NO. : 11/748858
DATED : August 25, 2009
INVENTOR(S) : Singh et al.

It is certified that error appears in the above-identified patent and that said Letters Patent is hereby corrected as shown below:

Col. 26, lines 42-63, Claim 13, should read: A process according to claim 2 wherein said compound of formula IIa is produced by a process of reacting a compound of formula Va:

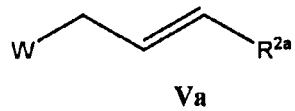

Va wherein W is chosen from bromine, chlorine, iodine, and triflate; with an aniline of formula VIa:

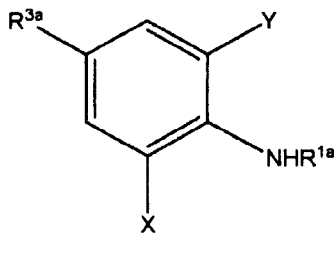

VIa in the presence of a base.

Signed and Sealed this

Twenty-second Day of June, 2010

David J. Kappos
*Director of the United States Patent and Trademark Office*